United States Patent [19]

Virdalm

[11] Patent Number: 4,857,327

[45] Date of Patent: Aug. 15, 1989

[54] METHOD FOR SUPPRESSING STATES OF ILLNESS IN THE DIGESTIVE SYSTEM

[76] Inventor: Carl A. Virdalm, Starevagen 10, 872 00 Kramfors, Sweden

[21] Appl. No.: 858,783

[22] Filed: May 2, 1986

Related U.S. Application Data

[63] Continuation-in-part of Ser. No. 668,770, Oct. 16, 1984, abandoned.

[30] Foreign Application Priority Data

Feb. 16, 1983 [SE] Sweden ............................... 8300847

[51] Int. Cl.$^4$ ...................... A61K 35/78; A61K 31/35
[52] U.S. Cl. ................................ 424/195.1; 514/456; 514/867
[58] Field of Search ..................... 424/195.1; 514/456, 514/867

[56] References Cited

FOREIGN PATENT DOCUMENTS 3027933 2/1981 Fed. Rep. of Germany .

OTHER PUBLICATIONS

Lietti et al., Arzneim-Frosch 26:829–872, 1976.
Poufrat, Plandes Méd. at Phytother, 11:143–151, 1977.
Pourat et al., Chim Therap. 2:33–38, 1967.

*Primary Examiner*—John W. Rollins
*Attorney, Agent, or Firm*—William A. Drucker

[57] ABSTRACT

A preparation for suppressing states of illness in the digestive system which contains cellulose, esculent organic acids and anthocyanins, the preparation being substantially free from or containing a proportionately small amount of components that form a nutriment for micro-organisms. For production of the preparation, the main portion of the pulp flesh and preferably also pips, if any, are removed from berries or fruits naturally containing cellulose, organic acids and anthocyanins, after which the remainder is utilized as or for the production of the preparation.

20 Claims, 1 Drawing Sheet

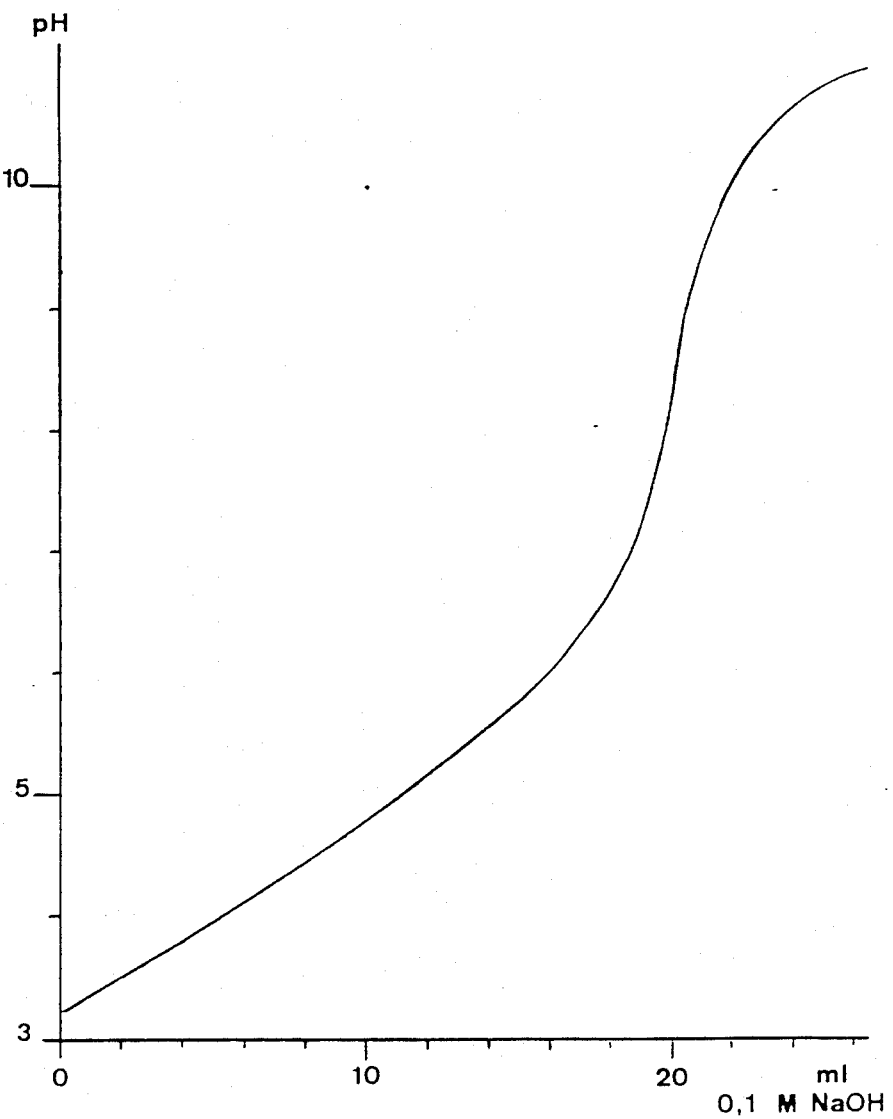

METHOD FOR SUPPRESSING STATES OF ILLNESS IN THE DIGESTIVE SYSTEM

REFERENCE TO RELATED APPLICATIONS

This application is a continuation-in-part of Ser. No. 668,770 filed Oct. 16, 1984 now abandoned.

FIELD OF THE INVENTION AND PRIOR ART

An object of the invention is a preparation for suppressing states of illness caused by microorganisms in the digestive system.

When treating illnesses occurring in the stomach that cause indisposition, vomiting and diarrhea and that in serious cases can lead to catarrhs or inflammations in the intestines, for example enterocolitis, for example dried bilberries and bilberry soup are used (Medicinsk Örthandbok by Hans Bertil, June 1977, p. 155-157). The pharmaceutical effect thereof is however rather poor.

When treating such illnesses, activated carbon or fasting is further resorted to. The activated carbon will absorb exotoxins from pathogenic microorganisms but has no influence on those microorganisms that cause the state of illness. Neither has the carbon any favorable influence for reinstating the normal flora of bacteria or any curative effect on the mucous membranes of the stomach and intestines. Antibiotics as penicillin and streptomycin can certainly be used but are subject to the disadvantage that they can give rise to injuries in the stomach and intestinal canal.

SUMMARY OF THE INVENTION

An object of the present invention is now to provide a preparation adapted to suppressing states of illness caused by microorganisms in the digestive system, that on the one hand is efficient, and on the other is free from a negative influence on humans or animals. This object is achieved through a preparation on the basis of berries or fruits.

DETAILED DESCRIPTION OF THE INVENTION

Pathogenic bacteria give off exotoxins which cause indisposition, vomiting, diarrhea and dizziness. Pathogenic microorganisms as bacteria, virus and fungi give of exotoxins which cause indisposition, vomiting, diarrhea and dizziness. The invention is based on the understanding that the exotoxins are proteins having an anionic as well as a cationic character and can accordingly through ionic change be absorbed by a macromolecular material, as cellulose, that contains anionic carboxyl groups, and polymeric anthocyanins, which are cationic through oxonium ion or carbonium ion in resonance with each other. By the fact that the preparation according to the invention, which is designed for oral administration, contains cellulose, the exotoxins will be absorbed in the cellulose and, in the preferred case when the preparation also contains anthocyanins, on the polymeric anthocyanins and thereby the exotoxins will be impeded from going into the organism and causing states of illness in the same. Instead the exotoxins will be carried along with the faeces out of the body. By the organic acids preferably comprised in the preparation, a check on the activity of the pathogenic bacteria will be achieved. By weak organic acids as citric acid, tartaric acid, succinic acid, malic acid and lactic acid comprised in the preparation a check on the activity of the pathogenic bacteria is achieved. These weak organic acids in fact have a toxic effect on primarily pathogenic bacteria in the pH range 1.5 to 5 (B. Norén, Mikrobiologi, p 116, 196, 200, 217, 218 and 224, Almqvist and Wiksell 1971) such as Salmonella, Shigella and *Vibrio cholerae* but have favorable effect on bacteria useful for the organism of families such as Lactobacillus and Bifidus. Certain studies suggest besides that anthocyanins also can have a certain bacteriocide action; the latter is now however at present unequivocally established.

Anthocyanins have more physiological effects that are of importance to counteract illnesses and harmful effects to the organism from, for example, exotoxins. Thus Lietti et al. (Arzneim.-Forsch., 26 (5), 829-832 (1976)) mention vascular protective and anti-inflammatory action of the same, Crippa et al. (the German publication 3 027 933) improvement in healing of wounds, Pourrat et al. (Plantes Médicin. 11, special No., 143-151 (1977)) considerable improvements in the condition of patients in artherioschlerosis, coronary chlerosis, cirrhosis, in the veins in connection with bleedings and when using anticoagulants, and Seeger (Ärtzliche Forschung 21 (2), 68-78 (1967)) carcinostatic action. The anthocyanins act as vitamin P having an effect twice as strong as routine and will reinforce the walls of the blood vessels and diminish the flow of blood. The acute toxicity is extraordinarily low. Pourrat mentions that the acute oral toxicity was not possible to establish as LD $0 \geqq 25$ g/kg for mouse and $\geqq 20$ g/kg for rat, Chim. Thérap., 2, 33-38 (1967).

By the fact that the preparation according to the invention thus contains cellulose and preferably organic acids as well as anthocyanins, a preparation is obtained having a bacteriostatic, healing, anti-inflammatory, bacteria flora normalizing and exotoxin absorbing effect. The anti-inflammatory effect counteracts oedema of the mucous membranes caused by toxins from the pathogenic microorganisms. Important in this connection is that the preparation is substantially free from or contains a proportionately small amount of components forming a nutriment for microorganisms as will be discussed in more detail hereinafter. Cellulose is nearly inert towards microorganisms.

The cellulose acts, except as an absorber of the exotoxins, as a carrier of the anthocyanins and the organic acids through the stomach and intestinal canal in such a manner that an effect will be obtained in all of the digestive system. The anthocyanins and the organic acids are thus comprised in the cellulose and are accordingly continually released during the transport through the system. In the duodenum the environment is slightly alcalic and accordingly favorable for growth of a plurality of pathogenic microorganisms as Salmonella and Vibrio, of which single individuals may have passed the strongly acid environment in the stomach without being killed. The organic acids in the preparation here counteract a growth of pathogenic microorganisms. In the jejunum and the large intestine the environment is again acid.

For the production of the preparation, a removal is effected of the main portions of the pulp flesh and preferably also the pips, if any, from berries or fruits that naturally contain cellulose, organic acids and anthocyanins, after which the remainder is utilized as or for the production of the preparation. The invention is based on the understanding that in berries and fruits, such as *Ribes nigrum* L (black currants), *Vaccinium myrtillus* L (bilberries), *Vaccinium vitis idaea* L (lingonberries), *Sambuccus nigra* (elderberries), *Vitis vinifera* (grapes)

etc., that contain varying amounts of, among other things, organic acids, pectins, tanning materials, sugar, anthocyanins and cellulose, the nutriment for the microorganisms, in fact the sugar, is found mainly in the pulp flesh. By separating according to the invention the main portion of the pulp flesh and using for the preparation the remainder in such a manner that the preparation will accordingly contain proportionately small amounts of components that form a nutriment for the microorganisms, a surprisingly great increase of the effect is obtained compared with that obtained when the patient is permitted to consume the pulp flesh as well. The remainder utilized for the preparation, that was substantially relieved of the pulp flesh, will thus have a substantially bacteriostatic effect. Possibly also the pectins and tanning materials contribute to the favorable effect of the preparation on the organism.

Pharmacological studies on a preparation made of berries from *Ribes nigrum* L (black currant) at 40% yield show no acute or subacute toxicity in oral doses up to 2000 mg/kg in mice.

The preparation has at a concentration of 4 mg/ml effect at the same level on contractions (antimotility activity) of stimulated guinea pig ileum on the same level as atropine sulfate at $9 \times 10^{-4}$ mg/ml, see table below:

| DRUG | BATH CONCENTRATION mg/ml | SPASMOLYTIC ACTIVITY, % |
| --- | --- | --- |
| Preparation | 4.0 | 76 |
| Atropine sulfate | $9 \times 10^{-4}$ | 80 |

The preparation elicities in a divided 2000 mg/kg i.m. dose 35% inhibition of cholera toxin-induced fluid accumulation in ligated intestinal loops of mice, which is about 40% of the antisecretory activity induced by the reference standard chlorpromazine, 4 mg/kg.

In an antimicrobial test a 2.5 mm inhibition zone representing inhibition to *Escherichia coli* growth was observed around discs that had been dipped in the most concentratred solution of the preparation, 250 mg/ml. It is estimated that about 50% of all so called tourist diarrheas are caused by pathogenic *Escherichia coli* bacterias.

By starting thus from naturally occurring berries and fruits, an opportunity is given to an economical production of the preparation. The removal of the pulp flesh is performed preferably by pressing the berries or fruits against a sieve having such a mesh size as to retain the skins or outer portions of the berries or fruits while the main portion of the pulp flesh and pips will pass through the apertures of the sieve. The pressing thus yields a remainder consisting of the skins and outer portions of the berries or fruits, in which there is found what is the object of the invention, in fact cellulose, organic acids and anthocyanins. The remainder amounts generally to about 40 percent by weight but can vary between 10 and 70 percent by weight.

The press cake obtained will next be dried. Anthocyanins lie near other easily oxidizable compounds as ascorbic acid and a d-α-tocopherol acetate (E-vitamin) on the redox scale and has as other phenol compounds a tendency to polymerize at an elevated temperature. The material resulting from the pressing that is to be used in the preparation should thus be dried at moderate temperatures, in fact at a temperature not exceeding 110° C. The drying temperature lies preferably between 40° and 110° C. at atmospheric pressure. The drying should preferably be performed at a temperature lower than 90° C. in vacuum; the temperature interval can be e.g., 35°–90° C.

The content of anthocyanins varies between different berries and fruits. Contents above 3 g/kg fresh berries are considered high and are found among other things in bilberries and black currants. The concentration of anthocyanins is usually higher in the skin than in the pulp flesh. Thus the major part in black currants is concentrated in the skin and is why the concentration is increased when the pulp flesh is separated.

The material resulting from the drying can subsequently be disintegrated through rubbing or grinding. The rubbed material can be used for the preparation of soups, while the ground material permits pressing tablets, which can either be used for the preparation of soups or be taken whole.

It is also possible to adopt the course of freezing the berries or fruits to −5° to −50° C., usually −20° C., after which the berries are made to pass through a sieve, e.g., a slot sieve, net sieve or bore sieve, where runners and other plant portions that do not essentially belong to the berry or fruit are separated. The berries or fruits are then thawed and pressed in a sieve having such a mesh size as to permit pulp flesh and pips to pass through. The press cake is rubbed and dried whereupon the procedure goes as described above.

A dose of the finished preparation can amount to 2–10 g but can be larger as well as smaller.

In the production of the preparation starting from berries or fruits through removal of the pulp flesh the content of anthocyanins will be at least 1 mg/g preparation, at most 60 mg/g and preferably 25 mg/g preparation, i.e., 2.5% by weight. In the previously mentioned publication of Crippa et al., 1 percent anthocyanins is stated for a salve for external application.

The sugar content of the previously mentioned berries usually ranges between 6 and 18% by weight. After removal of the pulp flesh it diminishes to a range of 0.5 and 4%, preferably around 1%, dependent on the kind of berry.

The effect of the preparation produced through the removal of the pulp flesh from berries or fruits can be reinforced by increasing the content of organic acids or anthocyanins or both through addition to the finished preparation. As esculant, organic acids can in that connection come into question, e.g., citric acid, succinic acid and lactic acid. Anthocyanins can be recovered from berries, as for example black currants, or fruits according to known methods as ion exchange according to the French patent specification 2, 299 385.

Through its high content of anthocyanins, the preparation according to the invention will also be able to be relied upon, except in acute stomach illnesses and diarrhea, in other states of illness in the stomach, as colon irritable, enteritis, colitis, enterocolitis and ulcer.

It is preferred to add to the preparation sodium sulphite that counteracts decomposition of the anthocyanins. The sodium sulphite addition amounts preferably to at most 5 percent by weight of the dry substance of the preparation.

EXEMPLIFICATION OF THE INVENTION

EXAMPLE 1

1 kg berries of *Ribes nigrum* L is pressed in a sieve having a mesh size of 2.5 mm, pulp flesh and pips passing through the sieve. In this process 410 g of press cake is obtained, that contains on the one hand the skins of the berries, and on the other a thin layer of pulp flesh next to the skin and having together a dry content of 19 percent. The press cake is dried at 90° C. to 94 percent dry content yielding 83 g dried material. The dried material is subsequently ground and sieved on a net having a mesh size of 2 mm. From the sieved material tablets of 600 mg are manufactured.

1 g of the ground product gives on slurrying in 100 ml distilled water a pH 3.2 at 37° C. Electrometric titration of the slurry with 0.1M sodium hydroxide solution gives a titre curve having an appearance according to the enclosed diagram, the acid contents on titration to some different pH give the corresponding mmol HCl according to the table below.

| pH | HCl, mmol/g |
| --- | --- |
| 4.0 | 0.5 |
| 5.0 | 1.1 |
| 6.0 | 1.6 |
| 7.0 | 1.9 |

The content of organic acids in the preparation corresponds to about 20 percent citric acid.

EXAMPLE 2

1 kg berries of *Vaccinium vitis idaea* L is frozen to 25°–20° C. The frozen berries pass a net sieve having a mesh size of 3 mm where small particles are separated. The berries are thawed and are subsequently pressed in a sieve having a mesh size of 2 mm in which process pips and pulp flesh are separated. In this process a 450 g press cake is obtained having a dry content of 24 percent. It is dried at 95° C. to a dry content of 93 percent resulting in 116 g of dried material. This is treated as in the previous example.

EXAMPLE 3

In the press cake according to Example 1, 3 percent by weight of sodium sulphite is admixed. The press cake is dried at 90° C. to 94 percent of dry content as in Example 1, after which also in what remains the procedure is done according to said example.

EXAMPLE 4

In the press cake according to Example 1, 5 percent by weight of citric acid and 5 percent by weight of lactic acid besides 1 percent by weight of anthocyanins are admixed. The press cake is dried at 90° C. to a dry content of 94 percent as in Example 1, after which in what remains the procedure is done according to said example.

What is claimed is:

1. A method of suppressing states of illness in the digestive system generated by pathogenic microorganism, said states of illness manifesting themselves in indisposition, vomiting and diarrhea or only diarrhea, with a preparation comprising cellulose, weak organic acids and anthocyanins, said preparation being produced by the steps of:
   (a) providing berries taken from the class consisting of *Ribes nigrus* L, *Vaccinium myrtillus* L, *Vaccinium vitis idaea* L, *Sambuccus nigra* and *Vitis vinifera;*
   (b) removing from the berries the main portion of the pulp flesh, which pulp flesh contains sugar which is a nutriment for microorganisms;
   (c) recovering the remainder of said berries amounting to from 10 to 70% by weight of the whole berries, said remainder constituting the skin and outer portion of the berries and thus containing from 1 to 60 mg/g of anthocyanins, giving a pH of from 1.5 to 5; and
   (d) utilizing the preparation recovered in step (c) to suppress illness in the digestive system.
2. The method according to claim 1 wherein the remainder is dried at a temperature between 40° and 110° C. at atmospheric pressure.
3. The method according to claim 2 wherein the remainder is disintegrated.
4. The method of claim 2 wherein the amount of sugar is from about 0.5 to about 4% by weight.
5. The method of claim 3 wherein the amount of sugar is from about 0.5 to about 4% by weight.
6. The method according to claim 1 wherein the remainder is dried at a temperature between 35° and 90° C. in vacuum.
7. The method according to claim 6 wherein the remainder is disintegrated.
8. The method of claim 7 wherein the amount of sugar is from about 0.5 to about 4% by weight.
9. The method of claim 6 wherein the amount of sugar is from about 0.5 to about 4% by weight.
10. The method according to claim 1 wherein the remainder is disintegrated.
11. The method of claim 10 wherein the amount of sugar is from about 0.5 to about 4% by weight.
12. The method of claim 1 wherein the amount of sugar is from about 0.5 to about 4% by weight.
13. The method according to claim 1 wherein said remainder is about 40% by weight of said whole berries and said anthocyanins amount to about 25 mg/g.
14. The preparation made by the process of claim 1.
15. The preparation made by the process of claim 2.
16. The preparation made by the process of claim 6.
17. The preparation made by the process of claim 10.
18. The preparation made by the process of claim 3.
19. The preparation made by the process of claim 7.
20. The preparation made by the process of claim 5.

* * * * *